United States Patent [19]

Lenz et al.

[11] Patent Number: 5,525,151
[45] Date of Patent: Jun. 11, 1996

[54] PROCESS FOR PREPARING A LOW-FAT, TRANSPARENT, STABLE OAT PROTEIN CONTAINING AQUEOUS SOLUTION AND PRODUCT THEREOF

[75] Inventors: Marvin K. Lenz, Algonquin; Steven D. Paisley, Fox River Grove, both of Ill.

[73] Assignee: The Quaker Oats Company, Chicago, Ill.

[21] Appl. No.: 417,504

[22] Filed: Apr. 4, 1995

Related U.S. Application Data

[63] Continuation of Ser. No. 15,504, Feb. 9, 1993, abandoned.

[51] Int. Cl.$^6$ ............................... A23L 11/00; C07K 3/02
[52] U.S. Cl. ..................... 106/154.1; 106/126; 426/481; 127/69; 127/70; 536/128
[58] Field of Search ................... 106/126, 154.1; 426/481; 127/69, 70; 536/128

[56] References Cited

U.S. PATENT DOCUMENTS

| | | | |
|---|---|---|---|
| 3,640,725 | 2/1972 | Sherba et al. | 99/17 |
| 4,990,344 | 2/1991 | Euber et al. | 426/28 |

FOREIGN PATENT DOCUMENTS 011208  6/1984  European Pat. Off. .

OTHER PUBLICATIONS

"Functinal Properties of Soy Protein Hydrolysates from a Continuous Ultrafiltration Reactor", W. Deeslie and M. Cheryan, Journal of Agricult. and FoodChem., vol. 36, No. 1, 1988, Washington, D.C., pp. 28–29.

*Primary Examiner*—David Brunsman
*Attorney, Agent, or Firm*—Lars S. Johnson; Mart C. Matthews

[57] ABSTRACT

The present invention relates to a process for preparing a low fat, transparent, stable oat protein containing aqueous solution comprising: preparing an initial stable, translucent aqueous suspension comprising water, an insoluble liquid fraction, a stable, soluble oat protein fraction, a soluble oat fat fraction, and a soluble oat carbohydrate fraction, wherein the oat fat is dissociated from the oat protein; removing the insoluble liquid fraction from the initial suspension; and recovering the stable, soluble oat protein fraction, soluble oat fat fraction, and soluble oat carbohydrate fraction in a final low fat, transparent, stable aqueous solution. The present invention further relates to the low fat, transparent, stable aqueous solution of the above process and a solid mixture containing a stable, soluble oat protein fraction in purified form which provides for a low fat, transparent, stable aqueous solution when put into solution in water.

18 Claims, No Drawings

5,525,151

PROCESS FOR PREPARING A LOW-FAT, TRANSPARENT, STABLE OAT PROTEIN CONTAINING AQUEOUS SOLUTION AND PRODUCT THEREOF

This is a continuation of application Ser. No. 08/015,504 filed on Feb. 9, 1993 now abandoned.

FIELD OF INVENTION

The present invention relates to a process for preparing a low fat, transparent, stable oat protein containing aqueous solution. The present invention also relates to the aqueous solution product of this process and a solid, purified oat protein containing mixture which when placed in solution provides for a transparent, stable oat protein containing aqueous solution.

BACKGROUND OF INVENTION

The oat seed from which the oat grain is taken comprises an oat hull and an oat groat. The oat hull serves as an outer covering of the groat. The oat groat is comprised of oat bran, including the pericarp and the aleurone layers, germ and endosperm. It is desirable to fractionate the oat groat into its soluble and insoluble fractions because each fraction of the groat has value in and of itself. Specifically of interest is the water soluble fraction of the groat which contains oat protein in a concentrated form. The oat protein in the fraction has many beneficial uses, including use in cosmetics and hair care and skin care formulations such as lotions, shampoos, creams and gels. However, aqueous compositions comprising oat protein fractions typically contain insoluble material, and as such are translucent and cannot be used in clear formulations, e.g., shampoos and beverages.

Also of interest are low fat, oat protein containing aqueous solutions and solid mixtures used to prepare aqueous solutions. These are useful as additives and protein supplements in low fat food items. Additionally, it is believed that such low fat oat protein containing compositions and mixtures will be more stable since they are likely less susceptible to rancidity. This is because they contain less fat for oxidation, which is the cause of rancidity. Unfortunately, such low fat oat protein containing compositions are also translucent, and therefore are not aesthetically pleasing when added to clear formulations such as beverages.

Furthermore, low fat, oat protein containing solutions have a greater concentration of protein as compared to full fat formulations. This translates into a greater protein yield, and the corresponding economy of efficient operation.

Given the foregoing, it would be desirable to prepare a transparent oat protein containing aqueous solution and solid mixture which is transparent when in solution, and which can be used in clear cosmetic and hair and skin care formulations. It would also be desirable if such aqueous solution and solid mixture fraction were low in fat as well. However, to date the known processes for preparing oat protein containing aqueous compositions and solid mixtures produce products which are not clear, and therefore cannot be used in such applications.

The present invention provides a low fat, transparent, stable oat protein containing solution, a low fat, solid stable oat protein containing mixture which provides a transparent aqueous solution upon rehydration, and a process for the preparation of such aqueous solution and solid mixture.

BACKGROUND ART

The art discloses oat fractionation processes and products of these processes.

The paper "Enzymic Solubilization of Cereal Proteins by Commercial Proteases", C. Nkonge and C. Ballance, Cereal Chem., Vol. 61, No. 4, pp. 316–320 (1984), teaches a method for obtaining an oat substrate having a nitrogen solubility of 90%. This paper discloses preparing aqueous slurries separately containing different varieties of grains, including oats. These slurries are rendered basic by the addition of a base. The aqueous, basic slurry is also treated with certain proteases for a period of 12 hours. This provides for the recovery of a soluble fraction of the grain from an insoluble fraction. In the case of the oat grain, a stable, oat protein containing solution appears to be prepared by this process.

U.S. Pat. No. 4,028,468, issued Jun. 7, 1977 to Hohner et al., discloses a process for fractionating oats comprising grinding dried, dehulled oat groats to form an oat flour containing a dense, fine fraction of regularly shaped particles and a light, coarse fraction of irregularly shaped particles, wherein the coarse fraction comprises oat bran, oat gum, oat protein and oat starch. The flour is recovered and the coarse and fine fractions are separated. The coarse fraction is then recovered and a heated, basic slurry containing the recovered coarse fraction is prepared. The heated, basic slurry is agitated to carry out an extraction and to form a bran fraction and a soluble fraction containing the oat gum, the oat protein and the oat starch. The oat bran is then recovered from the slurry while leaving the oat gum, the oat protein and the oat starch in the soluble fraction, thereby forming an alkaline extract of the soluble fraction. The alkaline extract is then chilled to a temperature in the range from above the freezing point of the alkaline extract to ambient temperature. The alkaline extract is chilled to form a precipitate of oat protein, which is removed along with the starch from the extract to form a supernatant liquid containing the oat gum to thereby recover the protein precipitate and the starch. The supernatant liquid is neutralized and heated to at least 90° C., after which the oat gum is recovered.

U.S. Pat. No. 4,448,790, issued May 15, 1984 to Sarkki et al., discloses a process for fractioning grain flour into at least three fractions of food quality including starch, protein and sugar fractions. The claimed process comprises slurrying grain flour into water; separating the resulting slurry into a heavier fraction containing ordinary grain starch and having a larger particle size and a lighter fraction containing about 15 to 40% of the dry substance of the flour which contains protein covered small particle starch; heating the lighter fraction to a temperature of at least 120° C. for a period of time sufficient for the protein network on the surface of the small particle starch to split and the starch to be gelatinized; cooling the lighter fraction to a temperature of 90° C. or lower and treating said lighter fraction simultaneously with alpha-amylase and betaglucanase; separating the resulting protein precipitate from the lighter fraction as a precipitate to obtain a clear fraction remaining after separating the precipitate; and saccharifying the clear fraction with amyloglucosidase or fungal amylase at a temperature of 55° C. or lower until the dextrose equivalent is at least 20 to 80.

U.S. Pat. No. 4,377,602, issued Mar. 22, 1983 to Conrad, discloses a process for the preparation of a hydrolyzed protein and starch product from whole grain and a product of the process. In the disclosed process in situ, enzymatically hydrolyzed protein and starch products are prepared from whole grain, said process comprising crushing whole grain and thereafter subjecting the crushed grain to a treatment which consists essentially of the following steps: subjecting said grain to an enzymatic treatment in an aqueous medium with an endopeptidase so as to transform substantially all water-insoluble proteins present in the grain to water-soluble protein products, which thereafter are filtered and recovered from the crushed grain as a clear filtrate containing protein products containing peptides and amino acid residues; and subjecting the remaining crushed grain to an enzymatic treatment in an aqueous medium with alpha-amylase followed sequentially by an amyloglucosidase, both enzymes being substantially free from other carbohydrate hydrolyzing enzymes so as to transform substantially all the water-insoluble starch fraction in the grain to water-soluble, degraded products of starch, wherein the amyloglucosidase is at a pH of between 4 to 4.5, so as to transform substantially all the water-insoluble starch fractions in the grain to glucose.

U.S. Pat. No. 4,282,319, issued Aug. 4, 1981 to Conrad, discloses a process for the preparation of a hydrolyzed protein and starch product from whole grain and a product of the process. In the disclosed process in situ, enzymatically hydrolyzed protein and starch products are prepared from whole grain, said process comprising crushing whole grain and thereafter subjecting the crushed grain to a treatment which consists essentially of the following steps: subjecting said grain to an enzymatic treatment in an aqueous medium with an endopeptidase so as to transform substantially all water-insoluble proteins present in the grain to water-soluble protein products, which thereafter are filtered and recovered from the crushed grain as a clear filtrate containing protein products containing peptides and amino acid residues; and subjecting the remaining crushed grain to an enzymatic treatment in an aqueous medium with at least one starch hydrolyzing enzyme so as to transform substantially all of the water-insoluble starch fraction in the grain to water-soluble, degraded products of starch, and wherein the starch hydrolyzing enzyme is amylase substantially free from other carbohydrate hydrolyzing enzymes.

The papers "Functional Properties of Oat Concentrate Treated With Linoleate or Trypsin", C. Ma, J. Inst. Can. Sci. Technol. Aliment., Vol. 18, No 1, pp. 79–84 (1985), and "Functional Properties of Oat Proteins Modified by Acylation, Trypsin Hydrolysis or Linoleate Treatment", C. Ma and D. Wood, JAOCS, Vol. 64, No. 12, pp. 1726–1731 (1987), teach that treating oat protein with the protease trypsin will break down about half of the protein and will result in a protein component having a solubility of between 40–60% within the pH range of 3–8. These papers do not teach how to make a protein that is completely stable against precipitation and insolubility. Furthermore, the dry powder prepared by the disclosed process is at most 60% soluble in the pH range of 3.5–8.0.

The paper "Some Functional and Nutritional Properties of Oat Flours as Affected by Proteolysis", R. Ponnampalam, G. Goulet, J. Amiot and G. Brisson, J. Agric. Food Chem., Vol. 35, No. 2, pp. 279–285 (1987), teaches a flour product having a nitrogen protein solubility of 50% maximum.

The papers: "Oat Protein Concentrate from a Wet Milling Process: Composition and Properties", J. Cluskey, Y. Wu, J. Wall and G. Inglett, Cereal Chem. 50(4), pp. 481–488 (1973); "Protein Isolate from High-Protein Oats: Preparation, Composition and Properties", Y. Wu, K. Sexson, J. Cluskey and G. Inglett, J. Food Sci., Vol. 42, No. 5, pp. 1383–1386 (1977); "Oat Protein Concentrates from a Wet Milling Process: Preparation", J. Cluskey, Y. Wu, J. Wall and G. Inglett, Cereal Chem. 50(4), pp. 481–488 (1973); and U.S. Pat. No. 4,089,848, issued May 16, 1978 to Bell et al.; all teach extracting oat protein from oat products using an alkaline extraction process In addition to these processes, oat protein containing products are commercially available For example, products Oat CI-40 and Oat CI-15 are available from Canamino, Inc., 118 Veterinary Road, Saskatoon, SK, Canada The Oat CI-40 product is described as a protein derived from oats which has a 40% protein content; is an odorless beige powder; is dispersible in a number of solvents; and increases viscosity when undergoing hydration. The Oat CI-15 product is described as a protein derived from oats which has a 15% protein content; is an odorless beige powder; is dispersible in a number of solvents; and increases viscosity when undergoing hydration. Both of these products can be used in hair care and skin care formulations such as lotions, shampoos, creams and gels However, the products described above and prepared by the processes described above all lack the transparency of the aqueous solution product of the present invention. Each of these described oat protein fractions is translucent while in suspension. Furthermore, most of these fractions are unstable and will precipitate out of solution if allowed to sit for a period of 1–2 days at cooler conditions. Refrigerating the composition containing the soluble oat protein fraction also causes the fraction to precipitate. Once the oat protein fraction has precipitated out of solution, it is incapable of being put back into solution. Even using a protease to attack the precipitated oat protein fraction will not render the precipitated protein soluble again.

As such, it would be desirable to produce a low fat, oat protein containing solution which is stable and transparent. It would also be desirable to produce a solid, low fat, oat protein containing mixture which can be dissolved in water from a dried or powdered state to produce a transparent and stable aqueous solution. It would also be desirable to provide a process for producing said low fat, transparent, stable oat protein containing aqueous solution. The oat protein containing solution product of the present invention possesses such properties.

It is therefore an object of the present invention to provide a soluble oat protein containing aqueous solution which is transparent and stable, even under cooler or refrigerated conditions.

It is another object of the present invention to provide a solid, low fat, oat protein containing mixture which can be dissolved in water from a dried or powdered state to produce a transparent and stable aqueous solution.

It is still another object of the present invention to provide a process for preparing such an oat protein containing aqueous solution and dried, purified, low fat oat protein containing mixture.

These objects are accomplished by the invention described herein.

Unless otherwise noted, all weight percentages herein are on a dry weight basis.

SUMMARY OF THE INVENTION

The present invention relates to a process for preparing a low fat, transparent, stable oat protein containing aqueous solution comprising:

a) preparing an initial stable, translucent aqueous suspension comprising water, an insoluble liquid fraction, a stable, soluble oat protein fraction, a soluble oat fat fraction, and a soluble oat carbohydrate fraction, wherein the oat fat is dissociated from the oat protein;

b) removing the insoluble liquid fraction from the initial suspension; and c) recovering the stable, soluble oat protein fraction, soluble oat fat fraction, and soluble oat carbohydrate fraction in a final low fat, transparent, stable aqueous solution.

The present invention further comprises the product of the above process.

The present invention also further comprises a solid, low fat, stable, soluble oat protein containing mixture in purified form which provides for a low fat, transparent, stable aqueous solution when put into solution in water.

DETAILED DESCRIPTION OF THE INVENTION

In the process of the present invention, an initial stable, translucent aqueous suspension comprising water, an insoluble liquid fraction, a stable, soluble oat protein fraction, a soluble oat fat fraction, and a soluble oat carbohydrate fraction is first prepared. The fractions contained in the initial suspension are fractions of an oat substrate, such as whole groats, oat flour, oat bran, and the like.

The initial suspension may be prepared in any manner known to those skilled in the art, provided the method employed results in an aqueous suspension wherein the soluble oat protein is stable and wherein the oat fat is dissociated from the oat protein. Of course, it would not make sense to prepare the initial suspension by separately adding the individual soluble and insoluble components to water, only to then separate out the insoluble fraction. As such, the initial suspension is typically prepared by fractionating an oat substrate into an insoluble solid fraction, an insoluble liquid fraction, a soluble oat protein fraction, a soluble oat fat fraction, and a soluble oat carbohydrate fraction, and separating out the solid fraction. The exact method is not critical to the present invention, provided that it produces the initial stable, translucent aqueous suspension described herein.

Since it is an object of the process of the present invention to obtain a final aqueous solution which contains a stable, soluble oat protein, it is desirable to obtain the maximum oat protein concentration practical in the final solution. This may be accomplished by maximizing the amount of stable, soluble oat protein present in the initial aqueous suspension. The soluble oat protein is in solution in the initial suspension, remains so throughout the process of the present invention, and is contained in the final aqueous solution of the present invention. Thus, it is preferred to have as great a protein concentration in the initial suspension as practical.

The initial stable, translucent aqueous suspension typically comprises from about 5% to about 35%, more typically from about 10% to about 30%, still more typically from about 20% to about 30% by weight insoluble liquid fraction; from about 10% to about 70%, more typically from about 25% to about 60%, still more typically from about 40% to about 50% by weight stable, soluble oat protein; from 0% to about 3%, more typically from 0% to about 2%, still more typically from 0% to about 1% by weight soluble oat fat; and from about 5% to about 30%, more typically from about 10% to about 25%, still more typically from about 15% to about 20% by weight soluble oat carbohydrate.

The insoluble liquid fraction is primarily insoluble oat fat. Therefore, when a defatted oat substrate is used in the preparation of the initial translucent, aqueous suspension, the concentration of insoluble liquid fraction in the initial suspension will be correspondingly reduced by the amount of fat removed to produce the defatted oat substrate.

When a defatted oat substrate is used to prepare the initial suspension, the suspension typically comprises from about 1% to about 5%, more typically from about 1% to about 4%, still more typically from about 1% to about 2% by weight insoluble liquid fraction; from about 20% to about 80%, more typically from about 40% to about 70%, still more typically from about 50% to about 60% by weight stable, soluble oat protein; from 0% to about 3%, more typically from 0% to about 2, more typically from 0% to about 1% by weight soluble oat fat; and from about 10% to about 40%, more typically from about 15% to about 35%, more typically from about 20% to about 30% by weight soluble oat carbohydrate.

The initial aqueous suspension of the present invention must be stable. Therefore, the initial soluble oat protein fraction contained in the initial suspension has to be stable as well. By stable, it is meant that the oat protein fraction will not precipitate out of solution, as typically happens with oat protein. Furthermore, when the aqueous solution of the present invention is dried, it produces a dried product comprising the soluble oat fractions already described herein. In the dried state, substantially all the resulting dried product, including the soluble oat protein fraction, will go into solution upon rehydration and form a stable solution. This is a function of the stability of the oat protein fraction. Once the oat protein fraction precipitates out of solution, the fraction is rendered substantially insoluble and will not go back into solution upon rehydration. This definition of stable applies to the initial aqueous suspension, as well as the purified, low fat, soluble oat fraction which forms the transparent aqueous solution upon rehydration, and the final low fat, transparent, stable oat fraction containing aqueous solution prepared by the process of the present invention.

This stability is accomplished by fractionating an oat substrate into an insoluble solid fraction, an insoluble liquid fraction, and a soluble fraction. The oat substrate is treated with protease during fractionation and prior to any separation of the insoluble solid fraction from the insoluble liquid fraction and soluble fractions.

One method useful, although not necessarily preferred, for preparing the initial translucent suspension of the present invention is disclosed in "Enzymic Solubilization of Cereal Proteins by Commercial Proteases", C. Nkonge and C. Ballance, Cereal Chem., Vol. 61, No. 4, pp. 316–320 (1984), the disclosure of which is incorporated herein by reference. Again, it is emphasized that the method of preparing the initial translucent aqueous suspension of the present invention is not critical to the process of the invention, and even though some methods may be advantageous over others, none are considered part of the process of the present invention. The following description of a method for preparing the initial translucent suspension is for illustrative purposes only.

In such a method, an aqueous slurry comprising water and an oat substrate is initially prepared.

The oat substrate can be in any form from which a soluble fraction can be recovered, can be defatted, and can be whole or size reduced. Examples of useful oat substrates include both hulled and dehulled whole oats, defatted whole oats, whole rolled oats, sliced oats, defatted sliced oats, oat flour, defatted oat flour, oat bran, defatted oat bran, oat meal, defatted oat meal, fine oat flour, defatted fine oat flour, oat flakes, defatted oat flakes, and mixtures thereof, with oat flour being preferred.

The oat substrate may be size reduced by any method known to those skilled in the art. Processes for size reducing typically utilize abrasion, shear, impact and compression force. Examples of equipment useful for the size reduction accomplished herein include, but are not limited to, grinders, cereal granulators, hammermills, pinmills, roller mills, ball mills, attrition mills, kibblers, air jet mills, and granulators.

The concentration of oat substrate in the prepared slurry typically ranges from about 1% to about 15%, more typically from about 5% to about 15%, still more typically from about 8% to about 12% by weight, based upon the total weight of the aqueous slurry.

Once the aqueous slurry is prepared, the oat substrate is fractionated into an insoluble solid fraction, an insoluble liquid fraction, and a soluble fraction, and the soluble fraction of the oat substrate is dissolved By dissolved, it is meant that the soluble fraction goes into solution in the water solvent and remains in solution Preferably, the solubility of the soluble oat protein fraction is at least about 70%, more preferably at least about 85%, still more preferably at least about 95% in water The solubility is determined in accordance with the nitrogen solubility method set forth in the paper "Protein Isolate from High Protein Oats: Preparation, Composition and Properties", Y. Wu, K. Sexson, J. Cluskey and G. Inglett, J. Food Sci., Vol. 42, No. 5, pp. 1383–1386 (1977).

The soluble fraction is dissolved by maintaining the slurry at a sufficient temperature and agitating the slurry, adding base to adjust the pH of the slurry to the basic range, and adding a protease enzyme to the slurry. These steps can he in any order, provided that they follow the preparation of the slurry and precede the separation of the insoluble solid fraction from the soluble fraction and insoluble liquid fraction of the oat substrate.

The slurry is maintained at a temperature and for a period of time sufficient, when combined with agitation and the addition of protease enzyme and base, to dissolve the soluble fraction of the oat substrate. The temperature is maintained at the necessary level by means known to those skilled in the art, typically by heating or cooling, the precise means depending upon factors such as the ambient temperature and necessary slurry temperature.

In the agitation step, the aqueous slurry is agitated, preferably by mechanical means, for a period of time sufficient, when combined with heating and the addition of base and protease enzyme, to dissolve the soluble fraction of the oat substrate. Generally, any method of agitation may be used. Examples of useful agitation methods include, but are not limited to, propeller stirrers, paddle blenders, and recirculating pumps.

The pH of the slurry is adjusted to the basic range by the addition of base. This is necessary to effect the extraction of the oat protein from the oat substrate. Generally, any food grade base known to those skilled in the art may be used. Examples of useful bases include, but are not limited to, sodium carbonate, sodium hydroxide, calcium hydroxide, ammonium hydroxide, and mixtures thereof.

The protease used is one which will render the soluble fraction stable and must be combined with the oat substrate prior to separation of the insoluble solid fraction from the insoluble liquid fraction and soluble fraction. A protease is not necessary to separate the oat substrate into soluble and insoluble fractions, as this can be accomplished solely by maintaining a proper slurry temperature and agitating the basic aqueous slurry. However, the protease is necessary for preparing a stable soluble oat protein fraction which will not precipitate out of solution upon storage, either in the initial aqueous suspension or the final, low fat, transparent solution of the present invention; which will go back into solution upon rehydration from a dried state; and which can be used in the initial aqueous suspension of the process of the present invention.

Protease enzymes which are known to work include, but are not limited to, proteases that have little or no amylase activity, such as Optimase® APL-440 and Opticlean® L-1000, both of which are available from Solvay Enzymes, located in Elkhart, Ind.; Alcalase®, available from Novo Nordisk, located in Wilton, Conn.; papain, and mixtures thereof.

The amount of protease enzyme necessary is that required to prepare a stable, soluble oat protein fraction, and will depend upon factors such as the amount of time available for the enzyme to react, the type or types of enzymes being use, and the pH of the slurry and degree and time of heating and agitation used. Typically, from about 0.1% to about 10.0% by weight, as a percentage of the oat substrate, of protease enzyme is combined with the aqueous slurry. The protease is typically allowed to react in a basic, heated and agitated aqueous slurry for a period of time in the range of from about 30 minutes to about 24 hours.

After the soluble fraction of the oat substrate has been dissolved in the slurry, the insoluble solid fraction is separated from the slurry. This separation may be accomplished by any method known to those skilled in the art. Examples of useful methods include, but are not limited to, centrifugation, filtering, passing the aqueous slurry through a molecular sieve, and allowing the aqueous slurry to sit in a settling pond for a sufficient period of time.

Typically the slurry is centrifuged at a gravitational force of at least about 2500 G's, more typically at least about 3500 G's, for a period of at least 1 minute, more typically at least 3 minutes.

This process produces a stable, translucent aqueous suspension comprising water, an insoluble liquid fraction, a stable, soluble oat protein fraction, a soluble oat fat fraction, and a soluble oat carbohydrate fraction, as already described herein. This aqueous suspension can be used as the initial aqueous suspension in the process of the present invention.

The oat substrate is desirably treated in some manner, typically during fractionation, to provide for a greater concentration of stable, soluble oat protein in the final transparent solution of the present invention. If an oat substrate is fractionated without treatment with a protease, after the insoluble solid fraction is removed the remaining suspension comprises a soluble carbohydrate fraction, an unstable soluble oat protein fraction, an insoluble liquid fraction which is primarily oat fat, and an insoluble liquid fraction comprising oat protein in association with oat fat. These insoluble liquids impart a translucency to the aqueous suspension, and therefore must be removed to obtain a transparent aqueous solution. However, if the insoluble liquid fraction comprising oat protein in association with oat fat is removed, then the yield of oat protein in the final solution will be undesirably low.

To obtain maximum yield of soluble oat protein in the final aqueous solution of the process of the present invention, the insoluble liquid fraction comprising oat protein in association with oat fat must be minimized. This is accomplished by dissociating the oat fat from the oat protein. Upon dissociation, an insoluble liquid oat fat containing fraction and a soluble, oat protein fraction are obtained. Therefore, in the initial aqueous suspension of the present invention, the oat protein should be substantially dissociated from the oat fat.

One method of achieving such dissociation is by treating the oat substrate with protease during fractionation, as already described herein. The amount of protease necessary to dissociate the oat protein from the oat fat is that already described herein for rendering the soluble oat protein fraction stable. The protease also has the added benefit of stabilizing the soluble oat protein, as already described herein.

After the initial translucent aqueous suspension is prepared, it is treated in a manner sufficient to remove the insoluble liquid fraction from the soluble fractions. Examples of methods useful for removing the insoluble liquid fraction from the suspension include, but are not limited to, physically separating the insoluble liquid fraction from the suspension, rendering the insoluble fraction soluble, and mixtures thereof. In a preferred embodiment, the initial aqueous suspension is concentrated and then subjected to a physical separation process.

Examples of concentration methods useful in the present invention include, but are not limited to, evaporation, reverse osmosis, freeze concentration, membrane filtration, ultrafiltration, and mixtures thereof, with evaporation being preferred, and evaporation utilizing heat and a vacuum being more preferred.

In more a preferred embodiment, the solids concentration of the initial translucent suspension is increased to at least about 5%, more preferably at least about 10%, still more preferably at least about 15% by weight, expressed as a percentage of the total aqueous suspension, and is heated to and/or maintained at a temperature of at least about 25° C., more preferably at least about 40° C., still more preferably at least about 50° C.

The physical separation of the insoluble liquid fraction can be accomplished by any method known to those skilled in the art. Examples of useful methods include, but are not limited to, microfiltration, centrifugation, settling, and mixtures thereof, with centrifugation and microfiltration being preferred and centrifugation followed by microfiltration being more preferred.

The centrifugation can be accomplished by any centrifuge equipment known to those skilled in the art. Examples of centrifugation equipment useful in the present invention include, but are not limited to, liquid/liquid disc separators, basket centrifuges, batch centrifuges, and decanters, with liquid/liquid disc separators being preferred.

Typically the suspension containing the insoluble liquid fraction is centrifuged at a gravitational force of at least about 2500 G's, preferably at least about 3000 G's, still more preferably at least about 3500 G's for a period of at least about 1 minute, preferably for at least about 2 minutes, still more preferably for at least about 3 minutes.

In a preferred centrifugation method, the suspension is maintained at a minimum temperature of about 5° C., preferably about 40° C., more preferably about 50×C, and then introduced into a liquid/liquid disc separator. The separator is operated at a minimum of about 2500 G's, preferably about 3000 G's, more preferably about 3500 G's. The residence time of the suspension in the separator is in the range of from about 1 to about 10 minutes, preferably from about 2 to about 5 minutes, more preferably from about 2 to about 3 minutes.

The microfiltration can be accomplished by any filtration equipment known to those skilled in the art. Examples of microfiltration equipment useful in the present invention include, but are not limited to, spiral membrane systems, tubular systems, ceramic membranes, and stainless steel membranes, with spiral wound membranes being preferred.

In a preferred microfiltration method, the suspension is heated to and/or maintained at a temperature of at least about 25° C., more preferably of at least about 40° C., still more preferably of at least about 50×C, and concentrated to a solids content in the range of from about 5% to about 30%, preferably about 5% to about 20%, still more preferably from about 10% to about 20% by weight. The heated and concentrated suspension is introduced into a spiral wound microfilter element. The filter is operated at a transmembrane pressure in the range of from about 5 to about 50 psi, preferably from about 10 to about 30 psi, more preferably from about 10 to about 20 psi.

The final transparent aqueous solution of the present invention typically comprises from about 30% to about 80%, more typically from about 40% to about 70%, more typically from about 50% to about 60% by weight stable, soluble oat protein; from 0% to about 5%, more typically from 0% to about 3%, still more typically from 0% to about 1% by weight soluble oat fat; and from about 10% to about 40%, more typically from about 15% to about 35%, still more typically from about 20% to about 30% by weight soluble oat carbohydrate, and typically contains a maximum of about 0.5%, preferably about 0.2%, still more preferably about 0.1% by volume of residual insoluble material.

To obtain a transparent aqueous solution, the size of any insoluble material present in the solution must be minimal, so as to not scatter or diffuse light. The maximum particle size of the residual insoluble material contained in the final, low fat, transparent aqueous solution of the present invention is typically about 1, preferably about 0.2, more preferably about 0.1 micron.

The present invention also includes the soluble aqueous solution product prepared by the process of the present invention, as already described herein.

The present invention also includes a final solid, i.e., dried, mixture comprising the stable, soluble oat protein fraction, soluble oat fat fraction, and soluble oat carbohydrate fraction as already described herein, including in the same relative concentrations, and has a maximum particle size when placed in solution as that already described herein for the aqueous solution. The solid mixture is obtained by drying the final aqueous solution of the present invention to a moisture level of no greater than about 12%, preferably about 10%, still more preferably about 8% by weight The soluble oat protein fraction contained in the purified solid mixture has a solubility of at least 70% preferably at least 85%, more preferably at least 95% in water The solubility is determined in accordance with the nitrogen solubility method set forth in the paper "Protein Isolate from High Protein Oats: Preparation, Composition and Properties", Y. Wu, K. Sexson, J. Cluskey and G. Inglett, J. Food Sci., Vol. 42, No. 5, pp. 1383–1386 (1977)

The final stable, soluble oat protein fraction of the process of the present invention, including in its dried form and when in solution as described above, may also be characterized by its molecular properties. The soluble oat protein has a molecular weight of less than about 30,000, preferably less than 10,000, more preferably less than 3,000. The molecular weight is a factor of the degree of treatment of the initial oat substrate with a protease enzyme during fractionation, as already described herein While not intending to be bound by theory, it is unexpected and surprising that a transparent, stable, oat protein containing solution can be prepared from a translucent suspension containing an insoluble liquid fraction and a soluble oat fraction by the process of the present invention. There is nothing that teaches or suggest that the fat in the form of an insoluble liquid can be separated from the soluble oat protein fraction, thereby producing a transparent, stable, oat protein containing aqueous solution. It is also unexpected and surprising that when in a dried state, the resulting oat protein containing mixture will produce a transparent stable solution upon rehydration.

In a preferred embodiment of the present invention, the resulting final stable, low fat, transparent aqueous solution is further treated to prevent or inhibit the growth of bacteria. This will provide a product which will be microbiologically stable. Microbiological stability is different from the phase stability that has already been discussed herein, and therefore can be stored and used by consumers over extended periods of time. The methods of treatment that can be used will be known by those skilled in the art. Examples of useful methods include, but are not limited to, lowering the water activity of the solution, for example by drying the solution to obtain a solid residue or adding a solvent such as propylene glycol; adding bactericides to the aqueous solution; acid treatment; lowering the solution temperature; and mixtures thereof; with lowering the water activity being preferred. In a more preferred embodiment, the water activity is lowered to a maximum level of about 0.65, more preferably about 0.60, still more preferably about 0.50.

The present invention is further illustrated, but not limited by, the following examples.

EXAMPLES

Example 1

The fine fraction of oat flour is slurried with water at a ratio of 1 to 10 parts by weight. The slurry is heated to 55°–60° C. and agitated. To the slurry, 2% soda ash ($Na_2CO_3$) by weight of oat flour is added to adjust the pH to 9.5–10.5. Finally, 1% protease enzyme (Optimase®) by weight of oat flour is added to the slurry. The slurry is held at 55°–60° C. with mild agitation for 1–2 hours, thereby fractionating the oat flour into an insoluble solid fraction, an insoluble liquid fraction, a soluble oat protein fraction, a soluble oat fat fraction, and a soluble oat carbohydrate fraction. The slurry is then centrifuged at 3200 G's for 3 minutes to separate the insoluble solid fraction, which produces an aqueous suspension containing an insoluble liquid fraction, a soluble oat protein fraction, a soluble oat fat fraction, and a soluble oat carbohydrate fraction. The soluble oat protein containing suspension is then neutralized with phosphoric acid to a pH of 6–6.5. The suspension is then concentrated in a falling film evaporator from a starting solids level of about 2–2.5% to 15–20% solids.

The concentrated suspension is then heated to 50°–60° C. and centrifuged using a liquid/liquid separator commonly used for separating cream from milk. From this separator, two streams are obtained—a light phase which contains 25–40% insoluble oil and a heavy phase which contains the soluble oat protein. Next, the heavy phase (oat protein containing suspension) is processed using a spiral-wound microfiltration system with a nominal pore size of 0.1 microns. The system is operated at 50°–55° C. with a transmembrane pressure of 10–20 psi. The solution that goes through the filter (the permeate) is then concentrated and spray-dried to give a tan powder with a protein content of 50–60% and a fat content of less than 1%. The powder can be mixed with water to make a 2–5% aqueous solution (by weight) which is transparent and which does not separate on standing.

Example 2

Oat flakes are slurried with water in a ratio of 1:12 parts by weight. The slurry is heated to 55°–60° C. and agitated. Two percent (2%) soda ash ($Na_2CO_3$) by weight of oat flakes is added to the slurry to adjust the pH to 9.5–10.5. At the same time, 0.5% protease enzyme (Optimase®) by weight of oat flour is added to the slurry. The slurry is held at 55°–60° C. with mild agitation for 1–2 hours, thereby fractionating the oat flour into an insoluble solid fraction, an insoluble liquid fraction, a soluble oat protein fraction, a soluble oat fat fraction, and a soluble oat carbohydrate fraction. The slurry is then centrifuged at 3200 G's for 2–3 minutes to separate the insoluble solid fraction, which produces an aqueous suspension containing an insoluble liquid fraction, a soluble oat protein fraction, a soluble oat fat fraction, and a soluble oat carbohydrate fraction. The soluble oat protein containing suspension is neutralized with any food acid such as phosphoric acid to a pH of 6–7. The suspension is then concentrated in a falling film evaporator from a starting solids level of 1.5–2.0% to 5–10% solids by weight. This aqueous suspension is heated to 45°–55° C. and fed to a spiral-wound microfilter with a nominal pore size of 0.1 micron. The system is operated at a transmembrane pressure of 10–20 psi. The solution that passes through the filter (permeate) contains the soluble oat protein. This permeate is concentrated in an evaporator and spray-dried to give a tan powder. The powder has a protein content of 50–60% and a fat content less than 1%. When this powder is rehydrated in water to make a 2–5% solution by weight, the solution is transparent and does not separate on standing. The yield of the oat protein powder is 10–15% based on the starting oat flour weight.

Example 3

Fine oat flour is slurried with water in a ratio of one part flour to ten parts water by weight. Two percent soda ash ($Na_2CO_3$) and 1% papain by weight of oat flour are added to the slurry, which is then heated to 55°–60° C., stirred, and held for 18 hours, thereby fractionating the oat flour into an insoluble solid fraction, an insoluble liquid fraction, a soluble oat protein fraction, a soluble oat fat fraction, and a soluble oat carbohydrate fraction. The slurry is then centrifuged at 3500 G's for 2–3 minutes to separate the insoluble solid fraction, which produces an aqueous suspension containing an insoluble liquid fraction, a soluble oat protein fraction, a soluble oat fat fraction, and a soluble oat carbohydrate fraction. The aqueous suspension is then neutralized with acid to a pH of 5–7, and concentrated to 8–15% solids using a reverse osmosis spiral-wound membrane system (Separatech® Membrane NF45, Separation Technology, Inc., St. Paul, Minn.). This suspension is then processed using a spiral-wound microfiltration system with a nominal pore size of 0.1 micron. The system is operated at 25°–30° C. with a transmembrane pressure of 10–20 psi. The solution that passes through the microfilter (permeate) contains the soluble oat protein and is transparent. This solution is evaporated using a falling film evaporator to 20–40% solids, and then spray dried. The spray-dried powder is tan in color and contains 5–10% moisture, 50–70% protein, 5–15% ash, and less than 1% fat. When this powder is rehydrated with water to make a solution, the solution is transparent, and does not separate on standing.

What is claimed is:

1. A process for preparing a low fat, transparent, stable oat protein containing aqueous solution comprising:
   a) preparing an initial stable, translucent aqueous suspension comprising water, an insoluble liquid fraction primarily comprising insoluble oat fat, a stable, soluble oat protein fraction, a soluble oat fat fraction, and a soluble oat carbohydrate fraction, wherein the oat fat is dissociated from the oat protein;
   b) removing the insoluble liquid fraction from the initial suspension; and
   c) recovering the stable, soluble oat protein fraction, soluble oat fat fraction, and soluble oat carbohydrate fraction in a final low fat, transparent, stable aqueous solution, wherein said final low fat, transparent, stable aqueous solution comprises from about 0% to about 1% by weight soluble oat fat.

2. A process according to claim 1 wherein the initial stable, translucent suspension comprises from about 10% to about 30% by weight insoluble liquid fraction; from about 25% to about 60% by weight stable, soluble oat protein; from 0% to about 2% by weight soluble oat fat; and from about 10% to about 25% by weight soluble oat carbohydrate.

3. A process according to claim 2 wherein the initial stable, translucent suspension comprises from about 20% to about 30% by weight insoluble liquid fraction; from about 40% to about 50% by weight stable, soluble oat protein; from 0% to about 1% by weight soluble oat fat; and from about 15% to about 20% by weight soluble oat carbohydrate.

4. A process according to claim 2 wherein the insoluble liquid fraction is removed from the suspension by concentrating the initial aqueous solution and physically separating the insoluble liquid fraction.

5. A process according to claim 4 wherein the initial aqueous suspension is concentrated to a solids content of at least about 10% by weight, expressed as a percentage of the total aqueous suspension.

6. A process according to claim 5 wherein the physical separation method is selected from the group comprising microfiltration, centrifugation, settling, and mixtures thereof.

7. A process according to claim 6 wherein the physical separation method comprises heating the suspension to a temperature of at least about 40° C. and centrifuging the suspension in a liquid/liquid separator operated at a minimum of 3,000 G's for a period in the range of from about 2 to about 5 minutes, followed by microfiltration.

8. A process according to claim 7 wherein the microfiltration is achieved by filtering the suspension in a spiral wound microfilter element operating at a transmembrane pressure in the range of from about 10 to about 20 psi.

9. A process according to claim 6 wherein the final transparent aqueous solution comprises from about 40% to about 70% by weight stable, soluble oat protein; from about 15% to about 35% by weight soluble oat carbohydrate, and contains a maximum amount of about 0.2% by volume of residual insoluble material.

10. A process according to claim 9 wherein the final aqueous solution comprises from about 50% to about 60% by weight stable, soluble oat protein; from about 20% to about 30% by weight soluble oat carbohydrate, and contains a maximum of about 0.1% by volume of residual insoluble material.

11. A process according to claim 1 wherein following separation of the insoluble liquid fraction from the soluble oat fraction, the final low fat, transparent, stable oat protein containing solution is stabilized to prevent the growth of bacteria.

12. A low fat, transparent, stable oat protein containing solution prepared by a method comprising:
   a) preparing an initial stable, translucent aqueous suspension comprising water, an insoluble liquid fraction primarily comprising insoluble oat fat, a stable, soluble oat protein fraction, a soluble oat fat fraction, and a soluble oat carbohydrate fraction, wherein the oat fat is dissociated from the oat protein;
   b) removing the insoluble liquid fraction from the initial suspension; and
   c) recovering the stable, soluble oat protein fraction, soluble oat fat fraction, and soluble oat carbohydrate fraction in a final low fat, transparent, stable aqueous solution, wherein said final low fat, transparent, stable aqueous solution comprises from 0% to about 1% by weight soluble oat fat.

13. A transparent, stable aqueous solution comprising water and from about 40% to about 70% by weight stable, soluble oat protein; from 0% to about 1% by weight soluble oat fat; from about 15% to about 35% by weight soluble oat carbohydrate, wherein the solution contains a maximum of about 0.2% by volume of insoluble material, and wherein the maximum particle size of the residual insoluble material contained in the final aqueous solution is 0.2 microns.

14. An aqueous solution according to claim 13 comprising water and from about 50% to about 60% by weight stable, soluble oat protein; from about 20% to about 30% by weight soluble oat carbohydrate, wherein the solution contains a maximum of about 0.1% by volume of insoluble material, and wherein the maximum particle size of the residual insoluble material contained in the final aqueous solution is 0.1 microns.

15. A solid, low fat oat protein containing mixture in a purified form comprising from about 10% to about 40% by weight soluble oat carbohydrate, from 0% to about 1% by weight soluble oat fat, and from about 40% to about 70% by weight stable, soluble oat protein, wherein said fraction has a maximum particle size of insoluble material in solution of about 0.2 microns and wherein said fraction provides a transparent aqueous solution when put into solution in water.

16. A solid oat protein containing mixture according to claim 15 wherein the soluble oat protein fraction has a solubility of at least about 85% in water.

17. A solid oat protein containing mixture according to claim 16 comprising from about 20% to about 30% by weight soluble oat carbohydrate, from 0% to about 1% by weight soluble oat fat, and from about 50% to about 60% by weight stable, soluble oat protein, wherein said fraction has a maximum particle size of insoluble material in solution of about 0.1 microns.

18. A solid oat protein containing mixture according to claim 17 wherein the oat protein fraction has a solubility of at least about 95% in water.

* * * * *